United States Patent [19]

Yamada

[11] Patent Number: 4,505,807

[45] Date of Patent: Mar. 19, 1985

[54] OXYGEN SENSOR

[75] Inventor: Tetsusyo Yamada, Nagoya, Japan

[73] Assignee: NGK Spark Plug Co., Ltd., Nagoya, Japan

[21] Appl. No.: 404,837

[22] Filed: Aug. 3, 1982

[30] Foreign Application Priority Data

Feb. 26, 1982 [JP]  Japan .............................. 57-27266[U]

[51] Int. Cl.³ ............................................. G01N 27/46
[52] U.S. Cl. ..................................... 204/425; 204/426;
204/427; 204/428; 204/429; 204/412; 29/620;
156/89; 264/61; 427/126.5
[58] Field of Search ................................. 204/424–429,
204/409, 412

[56]  References Cited

U.S. PATENT DOCUMENTS

| 3,791,937 | 2/1974 | Besson et al. ........................ 204/427 |
| 4,264,425 | 4/1981 | Kimura et al. ....................... 204/429 |
| 4,272,329 | 6/1981 | Hetrick et al. ....................... 204/1 T |
| 4,294,679 | 10/1981 | Maurer et al. ....................... 204/426 |
| 4,300,991 | 11/1981 | Chiba et al. ......................... 204/426 |
| 4,359,989 | 11/1982 | Masaki et al. ....................... 204/428 |

FOREIGN PATENT DOCUMENTS 56-130649 10/1981 Japan .

Primary Examiner—T. Tung
Attorney, Agent, or Firm—Fleit, Jacobson, Cohn & Price

[57]  ABSTRACT

The disclosed oxygen sensor includes three plate-like elements disposed in parallel and a heater, i.e., an oxygen pump element with electrodes and said heater disposed adjacent thereto, an oxygen concentration cell element with electrodes, and an insulating board disposed between the first two elements and having a hole bored therethrough at a position between the opposing electrodes of the first two elements so as to define a cavity therebetween, said insulating board further having at least one passage communicating said cavity to outside of said oxygen sensor.

16 Claims, 12 Drawing Figures

OXYGEN SENSOR

BACKGROUND OF THE INVENTION

1. Field of the Invention

This invention relates to an oxygen sensor for measuring the oxygen concentration in a gas such as an exhaust gas, and more particularly to an oxygen sensor which can very accurately determine the air-fuel ratio or the like of a gas being measured over a wide range.

2. Description of the Prior Art

To improve the fuel cost and the cleanness of exhaust gas of an automobile engine, it has been proposed to run the engine with an intake air-fuel mixture of lean burn side, i.e., with an air-fuel ratio $\lambda$, or an excess air ratio, larger than the theoretical optimal value at unity ($\lambda = 1$). To this end, there is a need for an oxygen sensor which can accurately measure the air-fuel ratio of unity or larger than unity $\lambda \geq 1$. One example of such oxygen sensors of the prior art was disclosed in Japanese Patent Laying-open Publication No. 130,649/81 which was filed by the Ford Motor Company of the U.S.A.

The above-mentioned Ford's oxygen sensor uses two sintered plates of oxygen-ion-conductive solid electrolyte each of which has electrodes attached to opposite surfaces thereof. One of the sintered plates is used as an oxygen pump element while the other one of them is used as an oxygen concentration cell element. The oxygen pump element and the oxygen concentration cell element are attached to opposite surfaces of a cylindrical spacer so as to sandwich the sidewall of the cylindrical spacer by the two elements. The sidewall of the cylindrical spacer is made of a refractory material and has fine holes bored therein, so that an enclosed space is defined between the above-mentioned two elements while oxygen-diffusing holes are defined by said fine holes of the sidewall of the cylindrical spacer. The oxygen concentration of a gas can be electrically measured by placing the oxygen sensor in the gas, and applying an electric current through the oxygen pump element so as to pump out the oxygen from the above-mentioned enclosed space to the outside atmosphere or the gas being measured, while allowing diffusion of oxygen into the enclosed space through the oxygen-diffusing holes of the cylindrical spacer sidewall, until for instance an oxygen concentration ratio between the enclosed space and the outside atmosphere of the gas being measured reaches a certain stable value. The last mentioned oxygen concentration ratio is given by the oxygen concentration cell element as an output thereof, and the magnitude of the current applied to the oxygen pump element for pumping out oxygen corresponds to the oxygen concentration in the outside atmosphere of the gas being measured. This oxygen sensor uses the oxygen pump element and the oxygen concentration cell element which are separately formed, so that the output from the oxygen sensor has an advantage in that the dependence of the output thereof on the temperature of the outside atmosphere of the gas being measured is low.

However, the above-mentioned sensor of the prior art has shortcoming in that when the accuracy is to be further improved, a heater must be added so that the temperature of the oxygen sensor and the ambient temperature can be kept substantially at a constant level. The addition of such a heater results in a reduced thermal efficiency.

SUMMARY OF THE INVENTION

Therefore, an object of the present invention is to obviate the above-mentioned shortcomings of the oxygen sensors of the prior art such as the conventional oxygen sensor for measuring the air-fuel ratio, and to provide a novel oxygen sensor of simple construction which sensor has a heat-generating resistor for efficiently heating the sensor without affecting the accuracy of the measurement so as to ensure very accurate measurement of the oxygen concentration.

To fulfil the object, an oxygen sensor according to the present invention comprises an oxygen pump element having a first oxygen-ion-conductive solid electrolyte board with electrode layers attached to opposite surfaces at one end of the first board; an oxygen concentration cell element having a second oxygen-ion-conductive solid electrolyte board disposed in parallel to said first board, said second board having electrode layers attached to opposite surfaces at one end thereof in alignment with said electrode layers of said first board; an electrically insulating board inserted between said oxygen pump element and said oxygen concentration cell element, said insulating board having a hole bored therethrough so as to define a cavity by closing said hole with said electrode layers attached to opposing surfaces of the first board and the second board, and a passage formed through said insulating board so as to communicate said cavity to outside of the oxygen sensor; and an insulated heat-generating resistor disposed adjacent to said oxygen pump element so as to extend along periphery of said cavity, whereby said oxygen sensor is selectively heated to such a temperature that said oxygen concentration cell element measures a ratio between oxygen concentration in said cavity and oxygen concentration of a gas surrounding the outside of said oxygen sensor while said oxygen pump element causes oxygen diffusion therethrough between said cavity and the outside of the oxygen sensor.

BRIEF DESCRIPTION OF THE DRAWINGS

For a better understanding of the invention, reference is made of the accompanying drawings, in which.

Throughout different views of the drawings, 1, 21, 41 and 71 are oxygen concentration cell elements; 2, 22, 42 and 72 are oxygen pump elements; 3, 23, 43 and 73 are heater elements; 6 is an insulating coating; 8, 28, 37, 48, 57, 61, 78, 87 and 91 are holes; 9, 10, 11, 12, 29, 30, 31, 32, 49, 50, 51, 52, 79, 80, 81 and 82 are electrodes; 13, 33, 53 and 83 are heat-generating resistors; 16, 36, 56 and 92 are cavities; 8a, 37a, 37b, 37c, 61a, 61b, 61c and 91a are passages; 26 and 46 are insulating boards; 59 and 89 are intermediate board members; 101 is an oxygen sensor; 102 is a housing; 103 is ceramic adhesive; 104 is an annular holder plate; 105 is a cylindrical spacer; 106 is a metallic connector tube; 107 is heat-resisting inorganic adhesive material; 112 is an insulated cord; and 113 is a lead wire.

DESCRIPTION OF THE PREFERRED EMBODIMENTS

Figure 1:
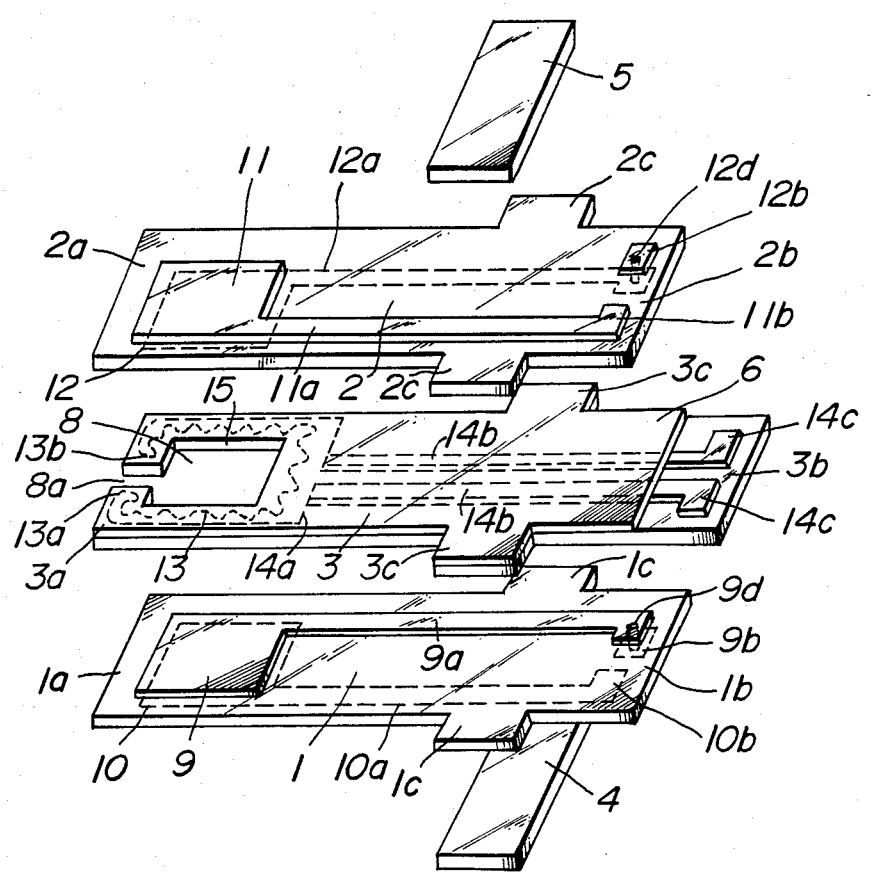
FIG. 1 is an exploded perspective view of a first embodiment of the oxygen sensor according to the present invention.
Figure 2:
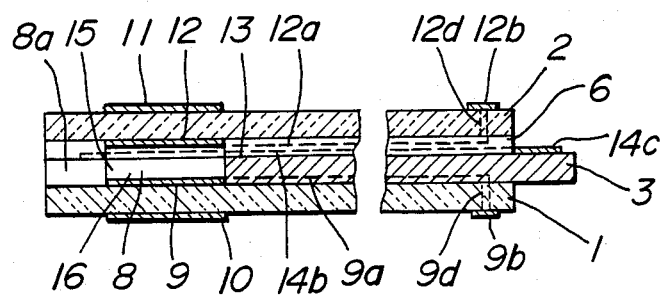
FIG. 2 is a sectional view of the embodiment of FIG. 1, taken along an axis in the length direction thereof.
Figure 3:
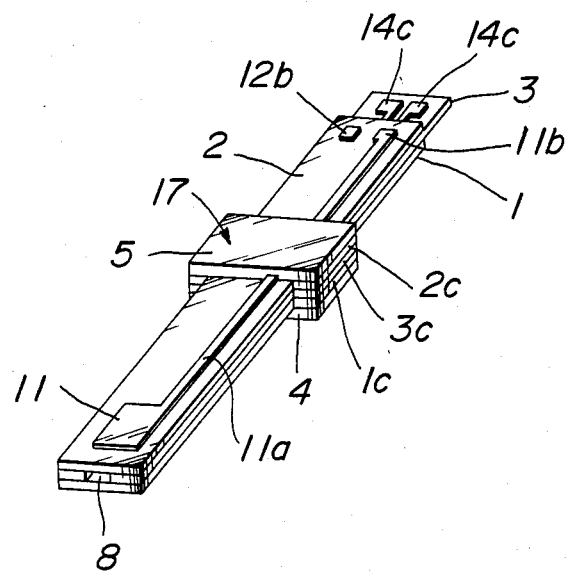
FIG. 3 is a perspective view of the assembled condition of the oxygen sensor of FIG. 1.

Referring to FIGS. 1 through 3 showing a first embodiment of the oxygen sensor according to the present invention, an oxygen concentration cell element 1 and an oxygen pump element 2 sandwich a heater element 3. The oxygen concentration cell element 1 has a rectangular solid electrolyte board with a front portion 1a and a rear portion 1b at longitudinal opposite ends thereof. A pair of aligned projections 1c extend in laterally opposite directions from the long sides of the electrolyte board in the proximity of the rear portion 1b thereof. Electrodes 9 and 10 are attached to opposite surfaces of the solid electrolyte board of the oxygen concentration cell element 1 at the front portion 1a thereof, so that the electrodes 9 and 10 are disposed back to back across the solid electrolyte board of the oxygen concentration cell element 1. In the illustrated embodiment, the electrodes 9 and 10 are square heat-resisting porous metallic layers which are deposited on the solid electrolyte board by a conventional porous layer depositing method, such as a thick layer depositing method or a thin layer depositing method.

A lead wire 9a made of a heat-resisting metallic strap layer extends straight from one corner of the square electrode 9 along the rear side thereof toward the rear portion 1b of the solid electrolyte board. A similar lead wire 10a made of a heat-resisting metallic strap layer extends straight from one corner of the other square electrode 10 along the rear side thereof toward the rear portion 1b of the solid electrolyte board. The two lead wires 9a and 10a emanate from opposite ends of the rear sides of the electrodes 9 and 10, as shown in FIG. 1. An outlet portion 10b is formed at the rear end of the lead wire 10a at the rear portion 1b of the solid electrolyte board, as shown in the figure. The rear end of the other lead wire 9a is electrically connected to an outlet portion 9b formed on the opposite side surface of the solid electrolyte board across a through hole 9d at the rear portion 1b thereof, as shown in FIG. 1. Consequently, the outlet portions 9b and 10b for the two electrodes 9 and 10 are both disposed on the same surface of the solid electrolyte board.

The oxygen pump element 2 also has a rectangular solid electrolyte board with substantially the same dimensions as those of the solid electrolyte board of the oxygen concentration cell element 1. A pair of aligned projections 2c extend in laterally opposite directions from the long sides of the electrolyte board in the proximity of the rear portion 2b thereof. Square electrodes 11 and 12 made of heat-resisting porous metallic layers are attached to the opposite surfaces of the solid electrolyte board at the front portion 2a thereof in a manner similar to the electrodes 9 and 10 of the oxygen concentration cell element 1. A lead wire 11a made of a heat-resisting metallic strap layer extends straight from one corner of the square electrode 11 along the rear side thereof toward the rear portion 2b of the solid electrolyte board. A similar lead wire 12a made of a heat-resisting metallic strap layer extends straight from one corner of the other square electrode 12 along the rear side thereof toward the rear portion 2b of solid electrolyte board. The lead wires 11a and 12a emanate from opposite ends of the rear sides of the electrodes 11 and 12, as shown in FIG. 1. An outlet portion 11b is formed at the rear end of the lead wire 11a at the rear portion 2b of the solid electrolyte board, as shown in the figure. The rear end of the lead wire 12a is electrically connected to an outlet portion 12b formed on the opposite side surface of the solid electrolyte board across a through hole 12d bored at the rear portion 2b thereof, as shown in FIG. 1. Consequently, the outlet portions 11b and 12b for the two electrodes 11 and 12 are both disposed on the same surface of the electrolyte board.

The solid electrolyte boards of the oxygen concentration cell element 1 and the oxygen pump element 2 are required to be oxygen-ion-conductive. Typical materials of the solid electrolyte boards are solid solutions of zirconia with 4–15 mole % of yttria, calcia or magnesia. Other oxygen-ion-conductive solid electrolytes which can be used in the present invention are solid solutions of cerium dioxide, thorium dioxide or hafnium dioxide; solid solutions of perovskite type oxides; and solid solutions of oxides of tervalent metals. The inventors used zirconia partially stabilized by yttria ($Y_2O_3$) for the solid electrolyte boards.

Heat-resisting metallic layers are used to form the electrodes 9, 10, 11 and 12, the lead wires 9a, 10a, 11a and 12a, and the outlet portions 9b, 10b, 11b and 12b on the surfaces of each of the solid electrolyte boards, and such heat-resisting metallic layers mainly consisting of platinum (Pt), ruthenium (Ru), palladium (Pd), rhodium (Rh), iridium (Ir), gold (Au) or silver (Ag). Preferably, the above-mentioned heat-resisting metallic layers of the electrodes, lead wires, and outlet portions are made by printing a paste containing the above-mentioned metallic element and the same green material. The inventors formed the above-mentioned heat-resisting metallic layers by preparing a paste consisting of platinum powder and 20 parts by weight of the same green material powder, printing the heat-resisting metallic layers with the paste thus prepared, and sintering the printed layers at the time of sintering said solid electrolyte boards of the elements 1 and 2. The heat-resisting metallic layers thus formed has a thickness of about 15 $\mu$m and a porosity of about 30%.

A heater element 3 has an electrically insulating rectangular plate made of alumina, spinel or the like. A pair of aligned porjections 3c extend in laterally opposite directions from the long sides of the insulating plate. The distance from the projections 3c to a front portion 3a of the insulating plate is the same as those of the two elements 1 and 2, but the distance from the projections 3c to a rear portion 3b of the insulating plate is longer than those of the two elements 1 and 2, as shown in FIG. 1. The width of the insulating plate of the heater element 3 is the same as the widths of the electrolyte boards of the elements 1 and 2. A hole 8 is bored through the insulating plate of the heater element 3 at the front portion 3a thereof. The position and size of the hole 8 are such that substantially the entire surfaces of the electrodes 9 and 12 of the oxygen concentration cell element 1 and the oxygen pump element 2 face toward each other across the hole 8, as can be seen from FIG. 1. A part of the insulating plate around the hole 8 of the heater element 3 is cut out so as to form a passage 8a which communicates the hole 8 to the outside of the oxygen sensor. The insulating plate has a heat-generating resistor 13 disposed on one side surface thereof along the periphery of the hole 8 in a waved form or in a linear form. Two end portions 13a and 13b of the heat-generating resistor 13 are disposed on opposing edges of the passage 8a and connected to two lead wires 14b through jumpers 14a. The two lead wires 14b extend from the end portions 13a and 13b of the heat-generating resistor 13 at the front portion 3a of the insulating plate to the rear portion 3b of the insulating plate where outlet portions 14c are formed at the rear ends of the lead wires 14b. The heat-generating resistor 13, the lead wires 14b, and the outlet portions 14c are made of heat-resisting metallic layers. For instance, the heat-generating resistor 13 can be formed by printing with a paste of heat-resisting anti-oxidation metal such as platinum (Pt) or rhodium (Rh), while the lead wires 14b and the outlet portions 14c can be formed by printing with a paste of heat-resisting metal which most commonly contains platinum (Pt), ruthenium (Ru), palladium (Pd), rhodium (Rh), iridium (Ir), gold (Au), or silver (Ag). The inventors formed the above-mentioned heat-resisting metallic layers by using a paste consisting of platinum powder and 20 parts by weight of the same green material powder.

An insulating coating 6 made of electrically non-conductive material is applied to that surface of the insulating plate of the heater element 3 on which the heat-generating resistor 13, the lead wires 14b, and the outlet portions 14c are formed, so as to insulate them. The material for the insulating coating is preferably the same as that of the insulating plate of the heater element 3, i.e., alumina or spinel is preferable because of their good adhesiveness when sintered and their freedom from thermal stress. In general, the insulating coating 6 has a thickness of about 50 μm.

To assemble the elements 1, 2 and 3 of the first embodiment into an oxygen sensor as shown in FIG. 2 and FIG. 3, preferably non-sintered green bodies of the oxygen concentration cell element 1, the heater element 3 with the insulating coating 6, and the oxygen pump element 2 are overlaid one above the other in said order and pressed together while aligning the front portions thereof, and coupling lugs 4 and 5 are attached by pressure to opposite surfaces of the overlaid projections 1c, 2c and 3c, so as to sandwich the projections between the coupling lugs. The thus overlaid green bodies with the coupling lugs applied thereto are sintered in open atmosphere so as to unite them into one unitary oxygen sensor.

Instead, the heater element 3 may be sintered by itself and then adhered to separately sintered oxygen concentration cell element 1 and the oxygen pump element 2 by using a heat-resisting inorganic adhesive or a paste of glass frit, so as to form an overlaid body. The overlaid body is then heated to bond the three elements into a unitary body. In this case, the heat-generating resistor 13 and the lead wires 14b may be made of metallic material with a high melting point such as tungsten (W).

Referring to FIG. 2 showing a longitudinal sectional view of the oxygen sensor of the first embodiment thus assembled and FIG. 3 showing a perspective view thereof, the oxygen sensor has a cavity 16 (e.g., with a section of 5 mm×5 mm and a thickness of 0.5 mm) surrounded by the electrode 9 (e.g., 5 mm×5 mm) of the oxygen concentration cell element 1, the electrode 12 (e.g., 5 mm×5 mm) of the oxygen pump element 2, and inner surfaces 15 of the hole 8 of the heater element 3. The cavity 16 communicates with the outside of the oxygen sensor through the passage 8a (e.g., with a section of 2 mm×0.5 mm and a length of 1 mm) and the heat-generating resistor 13 surrounds the periphery of the cavity (or the periphery of the hole 8). At the rear end of the oxygen sensor, the rear portion 3b of the heater element 3 sandwiched between the two elements 1 and 2 projects beyond the rear portions 1b and 2b of the latter, so as to expose the outlet portions 9b, 10b, 11b, 12b, 14c and 14c of the electrodes 9 through 12 and the lead wires 14b. A coupling portion 17 is formed between the central portion and the rear end of the oxygen sensor assembly, so as to facilitate the mounting of the assembled oxygen sensor in a sensor probe.

The inventors used a platinum heater with a capacity of 10 W at 12 V as the heat-generating resistor 13 surrounding the cavity 16, and such platinum heater proved to provide a sufficient heating capacity to the sensor for measuring the partial pressure in automobile engine exhaust gas. In a test of the oxygen sensor of the first embodiment of the invention, when oxygen was pumped out from the cavity 16 by applying an electric current of 0.02-3 mA through the oxygen pump element 2 while maintaining the output voltage of the oxygen concentration cell element 1 at a constant level of 20 mV, such range of the electric current through the oxygen pump element 2 was found to correspond to about 0.05-10% of oxygen concentration in the gas surrounding the outside of the oxygen sensor, which outside gas was being measured. The relationship between the current through the oxygen pump element 2 and the oxygen concentration in the gas being measured was found to be linear when being plotted on a logarithm-logarithm scale graph. During the test, the temperature of the oxygen sensor was kept at about 800° C.

In the first embodiment of the oxygen sensor which has been described above, the heater element 3 incorporated in the oxygen sensor acts to efficiently heat the entire oxygen sensor to bring about excellent temperature compensation. Besides, the heat-generating resistor 13 and the lead wires 14b through which the heating electric current flows are fully insulated from the other elements 1 and 2 by the insulating plate of the heater element 3 and the insulating coating 6 thereon, whereby the heating electric current never flows into the other elements 1 and 2 and no adverse effects are caused on the measuring accuracy by the heating electric current. The passage 8a having a cross section with a height corresponding to the thickness of the cavity 6 is large enough for preventing the passage 8a from being plugged during the service, which plugging leads to deterioration of the performance of the oxygen sensor, and for improving the response characteristics of the oxygen sensor.

Figure 4:
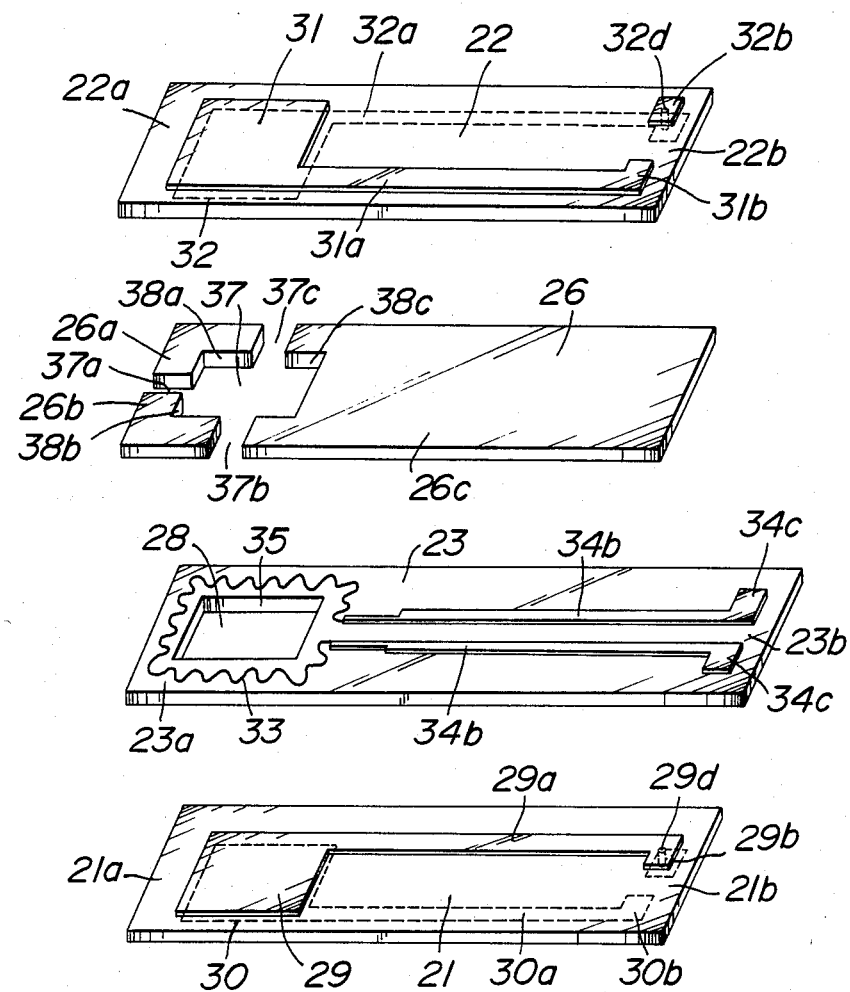
FIG. 4 is an exploded perspective view of a second embodiment of the oxygen sensor according to the present invention.

FIG. 4 shows a second embodiment of the oxygen sensor according to the invention. The oxygen sensor of FIG. 4 includes an oxygen concentration cell element 21, an oxygen pump element 22, a heater element 23, and an insulating board 26. The oxygen concentration cell element 21 has a rectangular solid electrolyte board with a front portion 21a and a rear portion 21b at opposite longitudinal ends thereof. Electrodes 29 and 30 are attached to the opposite surfaces of the solid electrolyte board of the oxygen concentration cell element 21 at the front portion 21a thereof, so that the electrodes 29 and 30 are disposed back to back across the solid electrolyte board of the oxygen concentration cell element 21. In the embodiment of FIG. 4 the electrodes 29 and 30 are square heat-resisting metallic layers. A lead wire 29a made of a heat-resisting metallic strap layer extends straight from one corner of the square electrode 29 along the rear side thereof toward the rear portion 21b of the oxygen concentration cell element 21. A similar lead wire 30a made of a heat-resisting metallic strap layer extends straight from one corner of the other square electrode 30 along the rear side thereof toward the rear portion 21b of the oxygen concentration cell element 21. The two lead wires 29a and 30a emanate from opposite ends of the rear sides of the electrodes 29 and 30, as shown in FIG. 4. An outlet portion 30b is formed at the rear end of the lead wire 30a at the rear portion 21b of the solid electrolyte board, as shown in the figure. The rear end of the lead wire 29a is electrically connected to an outlet portion 29b formed on the opposite side surface of the solid electrolyte board across a through hole 29d at the rear portion 21b, as shown in FIG. 4. Consequently, the outlet portions 29b and 30b for the two electrodes 29 and 30 are both disposed on the same surface of the solid electrolyte board.

The oxygen pump element 22 also has a rectangular solid electrolyte board with substantially the same dimensions as those of the solid electrolyte board of the oxygen concentration cell element 21. Square electrodes 31 and 32 made of heat-resisting metallic layers are attached to the opposite surfaces of the solid electrolyte board at the front portion 22a thereof in a manner similar to the electrodes 29 and 30 of the oxygen concentration cell element 21. A lead wire 31a made of a heat-resisting metallic strap layer extends straight from one corner of the square electrode 31 along the rear side thereof toward the rear portion 22b of the oxygen pump element 22. A similar lead wire 32a made of a heat-resisting metallic strap layer extends straight from one corner of the other square electrode 32 along the rear side thereof toward the rear portion 22b of the oxygen pump element 22. The lead wires 31a and 32a emanate from opposite ends of the rear sides of the electrodes 31 and 32, as shown in FIG. 4. An outlet portion 31b is formed at the rear end of the lead wire 31a at the rear portion 22b of the oxygen pump element 22, as shown in the figure. The rear end of the lead wire 32a is electrically connected to an outlet portion 32b formed on the opposite side surface of the solid electrolyte board across a through hole 32d bored at the rear portion 22b thereof, as shown in FIG. 4. Consequently, the outlet portions 31b and 32b for the two electrodes 31 and 32 are both disposed on the same surface of the solid electrolyte board.

The solid electrolyte boards of the oxygen concentration cell element 21 and the oxygen pump element 22 of the second embodiment are made of similar oxygen-ion-conductive solid electrolyte to that of the first embodiment of FIG. 1.

The electric conductive members deposited on the surfaces of the solid electrolyte boards, such as the electrodes 29, 30, 31, 32, the lead wires 29a, 30a, 31a, 32a and the outlet portions 29b, 30b, 31b and 32b, are formed by the same method as that of the first embodiment with the same material as that of the first embodiment.

The heater element 23 has an electric insulating plate made of alumina or spinel. The width of the insulating plate is the same as those of the other two elements 21 and 22, but the length of the insulating plate is somewhat longer than those of the elements 21 and 22. A hole 28 is bored through the insulating plate of the heater element 23 at the front portion 23a thereof. The position and size of the hole 28 are such that substantially the entire surfaces of the electrodes 29 and 32 of the oxygen concentration cell element 21 and the oxygen pump element 22 are aligned with the hole 28, as can be seen from FIG. 4. The insulating plate has a heat-generating resistor 33 disposed on one side surface thereof along the periphery of the hole 28 in a waved form or in a linear form. Two end portions of the heat-generating resistor 33 are connected to two lead wires 34b in the proximity of the rear side of the hole 28. The two lead wires 34b extend to the rear portion 23b of the insulating plate where outlet portions 34c are formed at the rear ends of the lead wires 34b. The above-mentioned heat-generating resistor 33, the lead wires 34b, and the outlet portions 34c are all formed by the same method as that for forming the corresponding parts of the first embodiment with the same heat-resisting metallic layers as those of the corresponding parts of the first embodiment.

The insulating board 26 has an electric insulating plate made of alumina or spinel. The width of the insulating board 26 is the same as the widths of the other three elements 21, 22 and 23, while the length of the insulating board 26 is the same as that of the oxygen concentration cell element 21. A hole 37 is bored through the entire thickness of the front portion of the insulating board 26 at a position corresponding to both the electrode 32 of the oxygen pump element 22 and the hole 28 of the heater element 23, and the size of the hole 37 corresponds to those of the electrode 32 and the hole 28. Three passages 37a, 37b and 37c are formed by cutting off three portions of the periphery of the hole 37 of the insulating board 26, so that the insulating board 26 consists of three separate pieces 26a, 26b and 26c, as shown in FIG. 4.

Figure 5:
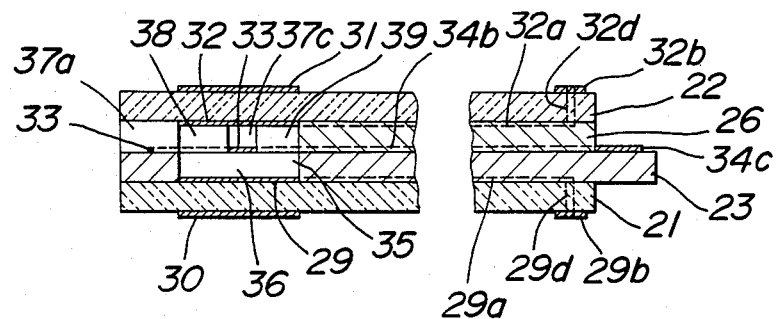
FIG. 5 is a sectional view of the embodiment of FIG. 4, taken along an axis in the length direction thereof.

To assemble the elements 21, 22, 23 and 26 of the second embodiment into an oxygen sensor as shown in FIG. 5, preferably non-sintered green bodies of the oxygen concentration cell element 21, the heater element 23, the insulating board 26, and the oxygen pump element 22 are overlaid one above the other in said order and pressed together while aligning the front portions thereof, and the thus overlaid green bodies are sintered so as to unite them into one unitary sensor.

Referring to FIG. 5 showing a longitudinal sectional view of the oxygen sensor of the second embodiment, the oxygen sensor has a cavity 36 (e.g. with a section of 5 mm × 5 mm and thickness of 1 mm) surrounded by the electrode 29 (e.g., 5 mm × 5 mm) of the oxygen concentration cell element 21, the electrode 32 (e.g., 5 mm × 5 mm) of the oxygen pump element 22, the inner surfaces 35 of the hole 28 of the heater element 23, and the inner surfaces 38a, 38b, 38c of the hole 37 of the insulating board 26. The cavity 36 communicates with the outside of the oxygen sensor through the passages 37a, 37b and 37c (e.g., each passage having a section of 1 mm × 0.5 mm and a length of 1 mm), and the heat-generating resistor 33 surrounds the periphery of the cavity 36 (or the periphery of the hole 28). At the rear end of the oxygen sensor, the rear portion 23b of the heater element 23 projects beyond the rear ends of the other elements, so as to expose the outlet portions 29b, 30b, 31b, 32b, 34c and 34c of the electrodes 29 through 32 and the lead wires 34b.

In a test of the second embodiment of the oxygen sensor, when the oxygen was pumped out from the cavity 36 by applying an electric current of 0.025–5 mA through the oxygen pump element 22 while maintaining the output voltage of the oxygen concentration cell element 21 at a constant level of 20 mV, such range of the electric current through the oxygen pump element 22 corresponded to about 0.05–10% of oxygen concentration in the gas surrounding the outside of the oxygen sensor which outside gas was being measured. The relationship between the current through the oxygen pump element 22 and the oxygen concentration in the gas being measured was found to be linear when plotted on a logarithm-logarithm scale graph. During the test, the temperature of the oxygen sensor of the second embodiment was kept at about 800° C.

In the second embodiment of the oxygen sensor described above, the heater element 23 incorporated in the oxygen sensor acts to efficiently heat the entire oxygen sensor to bring about excellent temperature compensation. Besides, the heat-generating resistor 33 and the lead wires 34b through the heating electric current flows are fully insulated from the other elements 21 and 22 by the insulating board 26 and the insulating plate of the heater element 23, whereby the heating electric current never flows into the other elements 21 and 22, and no adverse effects are caused on the measuring accuracy by the heating electric current. The three passages 37a, 37b and 37c provide openings in three directions toward the outside of the oxygen sensor, so that uniform oxygen diffusion between the cavity 36 and the outside of the oxygen sensor is ensured, whereby the response of the oxygen sensor is improved for enabling accurate measurement of the oxygen concentration.

Figure 6:
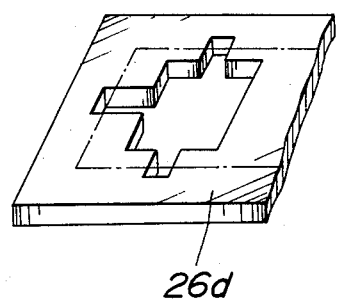
FIG. 6 is a fragmentary perspective view of an insulating board to be used in the second embodiment.

When the oxygen sensor of the second embodiment is assembled by overlaying elements thereof, the insulating board 26 consisting of three separate parts may be used as described above, but the efficiency of the assembling operation may be improved by providing an outside fringe portion 26d connecting the three parts as shown in FIG. 6 with an increased dimension of the insulating board 26, which fringe portion may be cut off after the green sheet thereof is overlaid between the other elements 22 and 23.

Figure 7:
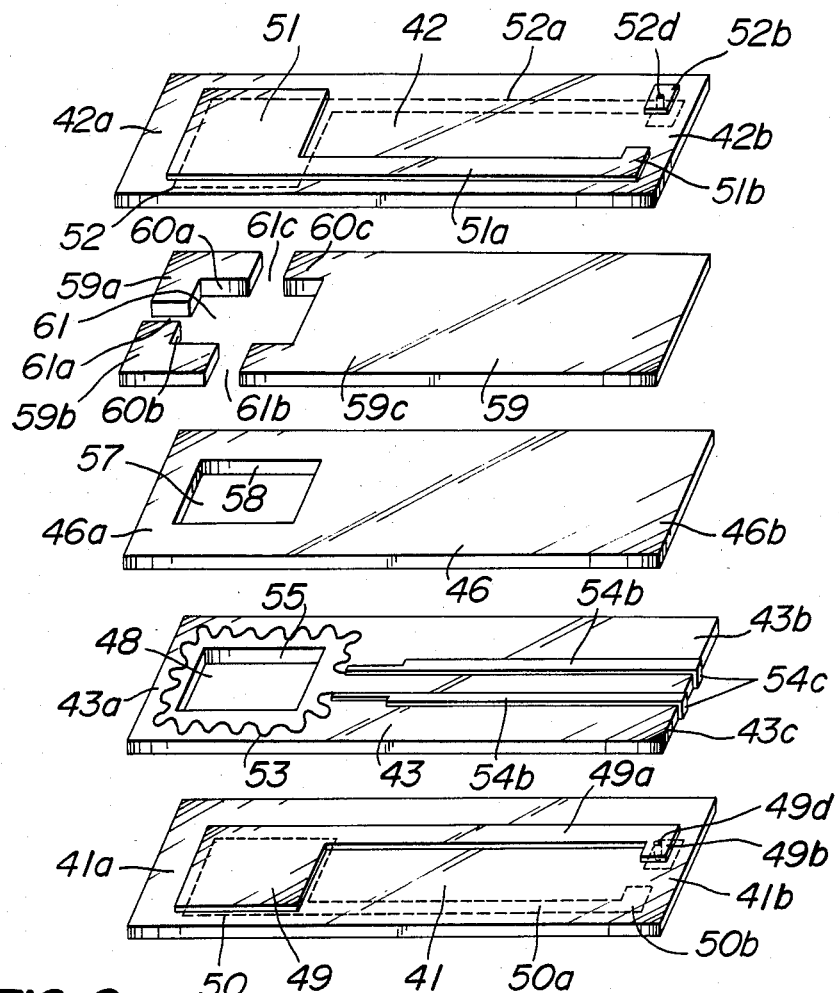
FIG. 7 is an exploded perspective view of a third embodiment of the oxygen sensor according to the present invention.

FIG. 7 shows a third embodiment of the oxygen sensor according to the present invention. The oxygen sensor of FIG. 7 includes an oxygen concentration cell element 41, an oxygen pump element 42, a heater element 43, an insulating board 46, and an intermediate board member 59.

The oxygen concentration cell element 41 has a rectangular solid electrolyte board with a front portion 41a and a rear portion 41b at opposite longitudinal ends thereof. Electrodes 49 and 50 are attached to the opposite surfaces of the solid electrolyte board of the oxygen concentration cell element 41 at the front portion 41a thereof, so that the electrodes 49 and 50 are disposed back to back across the solid electrolyte board of the oxygen concentration cell element 41. In the embodiment of FIG. 7, the electrodes 49 and 50 are square heat-resisting metallic layers. A lead wire 49a made of a heat-resisting metallic strap layer extends straight from one corner of the square electrode 49 along the rear side thereof toward the rear portion 41b of the oxygen concentration cell element 41. A similar lead wire 50a made of a heat-resisting metallic strap layer extends straight from one corner of the other square electrode 50 along the rear side thereof toward the rear portion 41b of the oxygen concentration cell element 41. The two lead wires 49a and 50a emanate from opposite ends of the rear sides of the electrodes 49 and 50, as shown in FIG. 7. An outlet portion 50b is formed at the rear end of the lead wire 50a at the rear portion 41b of the oxygen concentration cell element 41, as shown in the figure. The rear end of the lead wire 49a is electrically connected to an outlet portion 49b formed on the opposite side surface of the solid electrolyte board across a through hole 49d at the rear portion 41b, as shown in FIG. 7. Consequently, the outlet portions 49b and 50b for the two electrodes 49 and 50 are both disposed on the same surface of the solid electrolyte board.

The oxygen pump element 42 also has a rectangular solid electrolyte board with substantially the same dimensions as those of the solid electrolyte board of the oxygen concentration cell element 41. Square electrodes 51 and 52 made of heat-resisting metallic layers are attached to the opposite surfaces of the solid electrolyte board at the front portion 42a thereof in a manner similar to the electrodes 49 and 50 of the oxygen concentration cell element 41. A lead wire 51a made of a heat-resisting metallic strap layer extends straight from one corner of the square electrode 51 along the rear side thereof toward the rear portion 42b of the oxygen pump element 42. A similar lead wire 52a of a heat-resisting metallic strap layer extends straight from one corner of the other square electrode 52 along the rear side thereof toward the rear portion 42b of the oxygen pump element 42. The lead wires 51a and 52a emanate from opposite ends of the rear sides of the electrodes 51 and 52, as shown in FIG. 7. An outlet portion 51b is formed at the rear end of the lead wire 51a at the rear portion 42b of the oxygen pump element 42, as shown in the figure. The rear end of the lead wire 52a is electrically connected to an outlet portion 52b formed on the opposite surface of the solid electrolyte board across a through hole 52d bored at the rear portion 52b thereof, as shown in FIG. 7. Consequently, the outlet portions 51b and 52b for the two electrodes 51 and 52 are both disposed on the same surface of the solid electrolyte board.

The solid electrolyte board of the oxygen concentration cell element 41 and the oxygen pump element 42 of the third embodiment are made of similar oxygen-ion-conductive solid electrolyte to that of the first embodiment of FIG. 1.

The electric conductive members deposited on the surface of the solid electrolyte boards, such as the electrodes 49, 50, 51, 52, the lead wires 49a, 50a, 51a, 52a and the outlet portions 49b, 50b, 51b and 52b, are formed by the same method as that of the first embodiment with the same material as that of the first embodiment.

The heater element 43 has an electric insulating plate made of alumina or spinel. The width and the length of the insulating plate are the same as those of the other two elements 41 and 42. A hole 48 is bored through the insulating plate of the heater element 43 at the front portion 43a thereof. The position and the size of the hole 48 are such that substantially the entire surfaces of the electrodes 49 and 52 of the oxygen concentration cell element 41 and the oxygen pump element 42 are aligned with the hole 48, as can be seen from FIG. 7. The insulating plate has a heat-generating resistor 53 disposed on one side surface thereof along the periphery of the hole 48 in a waved form or in a linear form. Two end portions of the heat-generating resistor 53 are connected to two lead wires 54b in the proximity of the rear side of the hole 48. The two lead wires 54b extend to an edge surface 43c at the rear portion 43b of the insulating plate where outlet portions 54c are formed at the rear ends of the lead wires 54b. The above-mentioned heat-generating resistor 53, the lead wires 54b, and the outlet portions 54c are all formed by the same method as that for forming the corresponding parts of the first embodiment with the same heat-resisting metallic layers as those of the corresponding parts of the first embodiment.

The insulating board 46 has an electric insulating plate made of alumina or spinel. The width and length of the insulating board 46 are the same as the widths and lengths of the other three elements 41, 42 and 43. A hole 57 is bored through the entire thickness of the front portion 46a of the insulating board 46 at a position corresponding to both the electrode 52 of the oxygen pump element 42 and the hole 48 of the heater element 43, and the size of the hole 57 corresponds to those of the electrode 52 and the hole 48.

The intermediate board member 59 has a solid electrolyte board made of zirconia or the like, as in the case of the oxygen pump element 42. The width and the length of the intermediate board member 59 are the same as those of the other three elements 41, 42, 43 and the insulating board 46. As in the case of the insulating board 46, a hole 61 is bored through the entire thickness of the front portion thereof at a position corresponding to the hole 57, and the size of the hole 61 corresponds to that of the hole 57. Three passages 61a, 61b and 61c are formed by cutting off three portions of the periphery of the hole 61 of the intermediate board member 59, so that the intermediate board member 59 consists of three separate pieces 59a, 59b and 59c.

Figure 8:
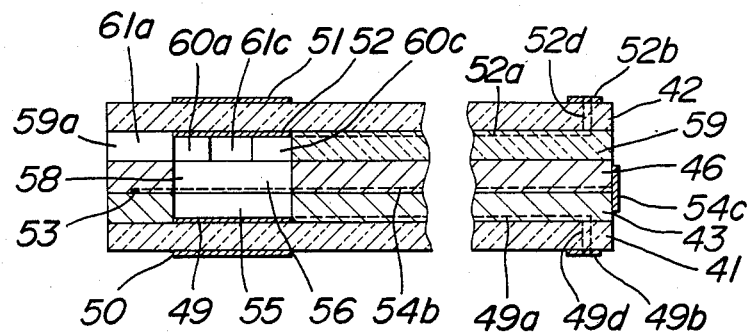
FIG. 8 is a sectional view of the embodiment of FIG. 7, taken along an axis in the length direction thereof.

To assemble the elements 41, 42, 43, the insulating board 46, and the intermediate board member 59 of the third embodiment into an oxygen sensor as shown in FIG. 8, preferably non-sintered green bodies of the oxygen concentration cell element 41, the heater element 43, the insulating board 46, the intermediate board member 59, and the oxygen pump element 42 are overlaid one above the other in said order and pressed together while aligning them, and the thus overlaid green bodies are sintered so as to unite them into one unitary oxygen sensor.

Referring to FIG. 8 showing a longitudinal sectional view of the oxygen sensor of the third embodiment, the oxygen sensor has a cavity 56 (e.g., with a section of 5 mm×5 mm and a thickness of 1.5 mm) surrounded by the electrode 59 (e.g., 5 mm×5 mm) of the oxygen concentration cell element 41, the electrode 52 (e.g., 5 mm×5 mm) of the oxygen pump element 42, the inner surfaces 55 of the hole 48 of the heater element 43, the inner surfaces 58 of the hole 57 of the insulating board 56, and the inner surfaces 60a, 60b and 60c of the hole 61 of the intermediate board member 59. The cavity 56 communicates with the outside of the oxygen sensor through passages 61a, 61b and 61c (e.g. each passage having a section of 1 mm×0.5 mm and a length of 1 mm), and the heat-generating resistor 53 surrounds the periphery of the cavity 56 (or the periphery of the hole 48). At the rear portion of the oxygen sensor, outlet portions 49b, 50b, 51b and 52b of the electrodes are provided, and the outlet portions 54c of the heat-generating resistor 53 of the heater element 43 are provided on the rear edge surface of the oxygen sensor. In the embodiment of FIGS. 7 and 8, the outlet portions 54c extend from the edge surface 43c of the heater element 43 to the edge surface of the insulating board 46.

In the case of the third embodiment, the relationship between the current through the oxygen pump element 42 and the oxygen partial pressure in the gas being measured proved to be substantially the same as that of the above-mentioned second embodiment.

In the oxygen sensor of the third embodiment as described above, the heater element 43 incorporated in the oxygen sensor acts to efficiently heat the entire oxygen sensor to bring about excellent temperature compensation. Besides, the heat-generating resistor 53 and the lead wires 54b thereof through which the heating electric current flows are fully insulated and embedded by the insulating plate of the heater element 43 and the insulating board 46, whereby the heating electric current never flows into the other elements 41 and 42, and no adverse effects are caused on the measuring accuracy by the heating electric current and the durability of the oxygen sensor is also improved. The three passages 61a, 61b and 61c provide openings in three directions toward the outside of the oxygen sensor, so that uniform oxygen diffusion between the cavity 56 and the outside of the oxygen sensor is ensured, whereby the response of the oxygen sensor is improved for enabling accurate measurement of the oxygen concentration.

Figure 9:
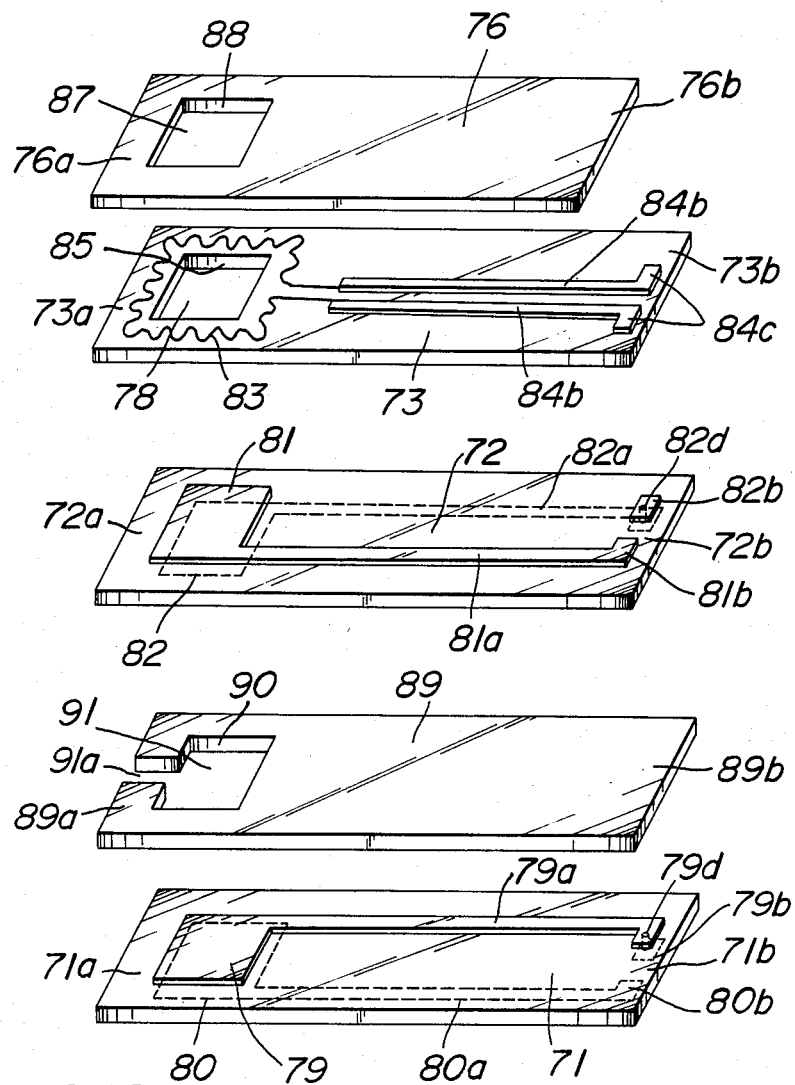
FIG. 9 is an exploded perspective view of a fourth embodiment of the oxygen sensor according to the present invention.

FIG. 9 shows a fourth embodiment of the oxygen sensor according to the present invention. The oxygen sensor of FIG. 9 includes an oxygen concentration cell element 71, an oxygen pump element 72, a heater element 73, a protective board 76 protecting the heater element 73, and an intermediate board member 89.

The oxygen concentration cell element 71 has a rectangular solid electrolyte board with a front portion 71a and a rear portion 71b at opposite longitudinal ends thereof. Electrodes 79 and 80 are attached to the opposite surfaces of the solid electrolyte board of the oxygen concentration cell element 71 at the front portion 71a thereof, so that the electrodes 79 and 80 are disposed back to back across the solid electrolyte board of the oxygen concentration cell element 71. In the embodiment of FIG. 9, the electrodes 79 and 80 are square heat-resisting metallic layers. A lead wire 79a made of a heat-resisting metallic strap layer extends straight from one corner of the square electrode 79 along the rear side thereof toward the rear portion 71b of the oxygen concentration cell element 71. A similar lead wire 80a made of a heat-resisting metallic strap layer extends straight from one corner of the other square electrode 80 along the rear side thereof toward the rear portion 71b of the oxygen concentration cell element 71. The two lead wires 79a and 80a emanate from opposite ends of the rear sides of the electrodes 79 and 80, as shown in FIG. 9. An outlet portion 80b is formed at the rear end of the lead wire 80a at the rear portion 71b of the oxygen concentration cell element 71, as shown in the figure. The rear end of the lead wire 79a is electrically connected to an outlet portion 79b formed on the opposite side surface of the solid electrolyte board across a through hole 79d at the rear portion 71b, as shown in FIG. 9. Consequently, the outlet portions 79b and 80b of the two electrodes 79 and 80 are both disposed on the same surface of the solid electrolyte board.

The oxygen pump element 72 also has a rectangular solid electrolyte board with substantially the same dimensions as those of the solid electrolyte board of the oxygen concentration cell element 71. Square electrodes 81 and 82 made of heat-resisting metallic layers are attached to the opposite surfaces of the solid electrolyte board at the front portion 72a thereof in a manner similar to the electrodes 70 and 80 of the oxygen concentration cell element 71. A lead wire 81a made of a heat-resisting metallic strap layer extends straight from one corner of the square electrode 81 along the rear side thereof toward the rear portion 72b of the oxygen pump element 72. A similar lead wire 82a of the heat-resisting metallic strap layer extends from one corner of the other square electrodes 82 along the rear side thereof toward the rear portion 72b of the oxygen pump element 72. The lead wires 81a and 82a emanate from opposite ends of the rear sides of the electrodes 81 and 82, as shown in FIG. 9. An outlet portion 81b is formed at the rear end of the lead wire 81a at the rear portion 72b of the oxygen pump element 72, as shown in the figure. The rear end of the lead wire 82a is electrically connected to an outlet portion 82b formed on the opposite side surface of the solid electrolyte board across a through hole 82d bored at the rear portion 72b thereof, as shown in FIG. 9. Consequently, the outlet portions 81b and 82b for the two electrodes 81 and 82 are both disposed on the same surface of the solid electrolyte board.

The solid electrolyte boards of the oxygen concentration cell element 71 and the oxygen pump element 72 of the fourth embodiment are made of similar oxygen-ion-conductive solid electrolyte to that of the first embodiment of FIG. 1.

The electric conductive members deposited on the surfaces of the solid electrolyte boards, such as the electrodes 79, 80, 81, 82, the lead wires 79a, 80a, 81a, 82a, and the outlet portions 79b, 80b, 81b and 82b, are formed by the same method as that of the first embodiment with the same material as that of the first embodiment.

The heater element 73 has an electric insulating plate made of alumina or spinel. The width of the insulating plate is the same as those of the other two elements 71 and 72, but the length of the insulating plate is somewhat shorter than the length of the other two elements 71 and 72. A hole 78 is bored through the entire thickness of the insulating plate of the heater element 73 at the front portion 73a thereof. The position and the size of the hole 78 correspond to those of the electrode 81 attached to the surface of the oxygen pump element 72. The insulating plate has a heat-generating resistor 83 disposed on one side surface thereof along the periphery of the hole 78 in a waved form or in a linear form. Two end portions of the heat-generating resistor 83 are connected to two lead wires 84b in the proximity of the rear side of the hole 78. The two lead wires 84b extend to the rear portion 73b of the insulating plate where outlet portions 84c are formed at the rear ends of the lead wires 84b. The above-mentioned heat-generating resistor 83, the lead wires 84b, and the outlet portions 84c are all formed by the same method as that for forming the corresponding parts of the first embodiment with the same heat-resisting metallic layers as those of the corresponding parts of the first embodiment.

The intermediate board member 89 has a plate which is either an electric insulating plate made of alumina or spinel or a solid electrolyte board similar to those of the oxygen concentration cell element 71 and the oxygen pump element 72. The width and length of the intermediate board member 89 are the same as those of the oxygen concentration cell element 71 and the oxygen pump element 72. A hole 91 is bored through the entire thickness of the front portion 89a of the intermediate board member 89 at a position corresponding to the electrode 79 attached to the above-mentioned oxygen concentration cell element 71, and the size of the hole 91 corresponds to that of the electrode 79. At least one passage 91a (only one is shown) is formed by cutting off a part of the front peripheral portion of the hole 91 of the intermediate board member 89, so as to communicate the hole 91 to the outside.

The protective board 76 has an electric insulating plate made of alumina or spinel. The width of the protective board 76 is the same as those of the three elements 71, 72, 73 and the intermediate board member 89, but the length of the protective board 76 is shorter than that of the heater element 73. A hole 87 is bored through the entire thickness of the front portion 76a of the insulating plate thereof at a position corresponding to the hole 78 of the heater element 73, and the size of the hole 87 corresponds to that of the hole 78.

Figure 10:
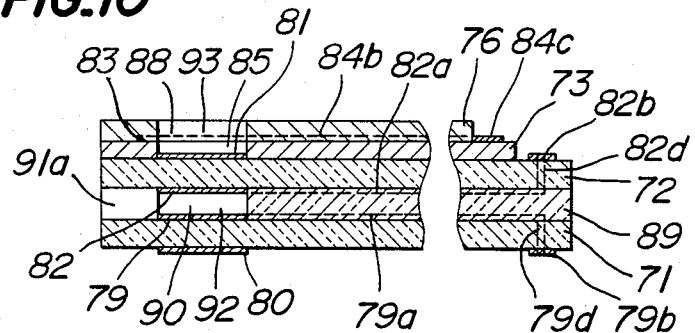
FIG. 10 is a sectional view of the embodiment of FIG. 9, taken along an axis in the length direction thereof.

To assemble the elements 71, 72, 73, the intermediate board member 89, and the protective board 76 of the fourth embodiment into an oxygen sensor as shown in FIG. 10, preferably non-sintered green bodies of the oxygen concentration cell element 71, the intermediate board member 89, the oxygen pump element 72, the heater element 73, and the protective board 76 are overlaid one above the other in said order and pressed together while aligning the front portions thereof, and then the thus overlaid green bodies are sintered as so to unite them into one unitary oxygen sensor.

Referring to FIG. 10 showing a longitudinal sectional view of the oxygen sensor of the fourth embodiment, the oxygen sensor has a cavity 92 (e.g., with a section of 5 mm×5 mm and a thickness of 0.5 mm) surrounded by the electrode 79 (e.g., 5 mm×5 mm) of the oxygen concentration cell element 71, the electrode 82 (e.g., 5 mm×5 mm) of the oxygen pump element 72, and inner surfaces 90 of the hole 91 of the intermediate board member 89. The cavity 92 communicates with the outside of the oxygen sensor through the passage 91a (e.g., a section of 2 mm×0.5 mm and a length of 1 mm). Besides, the oxygen sensor of the fourth embodiment has a flat rectangular opening 93, which opening is bottomed by the other electrode 81 attached to the oxygen pump element 72 and surrounded by the inner surface of the hole 78 of the heater element 73 and the inner surfaces 88 of the hole 87 of the protective board 76. The heat-generating resistor 83 surrounds the periphery of the hole 78 of the heater element 73. The extreme rear portion of the overlaid three element of the oxygen concentration cell element 71, the intermediate board member 89, and the oxygen pump element 72 has outlet portions 79b, 80b, 81b and 82b for the electrodes 79, 80, 81 and 82. A setback rear portion 73b of the heater element 73 carries the outlet portions 84c for the heat-generating resistor 83.

In the case of the fourth embodiment, the relationship between the current through the oxygen pump element 72 and the oxygen partial pressure in the gas being measured proved to be substantially the same as that of the above-mentioned first embodiment.

In the fourth embodiment of the oxygen sensor as described above, the heater element 73 incorporated in the oxygen sensor is disposed adjacent to the oxygen pump element 72, so that the oxygen pump element 72 is efficiently heated so as to effect excellent temperature compensation with little consumption of electric power. The supply of electric current to the oxygen pump element 72 is easy. The heater element 73 of the fourth embodiment is electrically insulated and more separated from the oxygen concentration cell element 71 as compared with other embodiments, so that adverse effect of the heater element 73 on the oxygen concentration cell element 71 is minimized.

Typical dimensions of the first through fourth embodiments described above are as follows: Each of the oxygen concentration cell elements, the oxygen pump elements, the heater elements, the insulating boards, the intermediate board members, and the protective boards generally has a length of about 5–70 mm, a width of about 3–10 mm, and a thickness of about 0.5 mm. Each of the holes bored through the above-mentioned elements and boards generally has a length of about 3–25 mm, a width of about 1–8 mm, and depth of about 0.5 mm. Each of the passages for communicating the cavity to the outside of the oxygen sensor generally has a height of about 0.5 mm, a width of about 0.5–3 mm (with a passage cross-sectional area of 1 mm$^2$ or more, preferably more than 3 mm$^2$) and a length of 1–3 mm. The peripheral wall of the above-mentioned holes generally has a thickness of about 1–3 mm. Each of the coupling lugs 4 and 5 used in the first embodiment generally has a length of about 2–30 mm, a width of 3–14 mm, and a thickness of about 0.5–1 mm. Each of the projections 1c, 2c and 3c of FIG. 1 has a foot width of about 5–30 mm, a projecting length of 0–2 mm, and a thickness of about 0.5 mm.

In the assembling method described above, ceramic green bodies of the elements and the board members are overlaid one above the other and then sintered so as to unite them into a unitary oxygen sensor, but it is also possible to sinter each of the elements and the board members separately and apply either a heat-resisting inorganic adhesive or a paste of glass frit so as to bond the elements and the board members in an overlaid fashion and then sinter the thus overlaid elements and board members.

Figure 11:
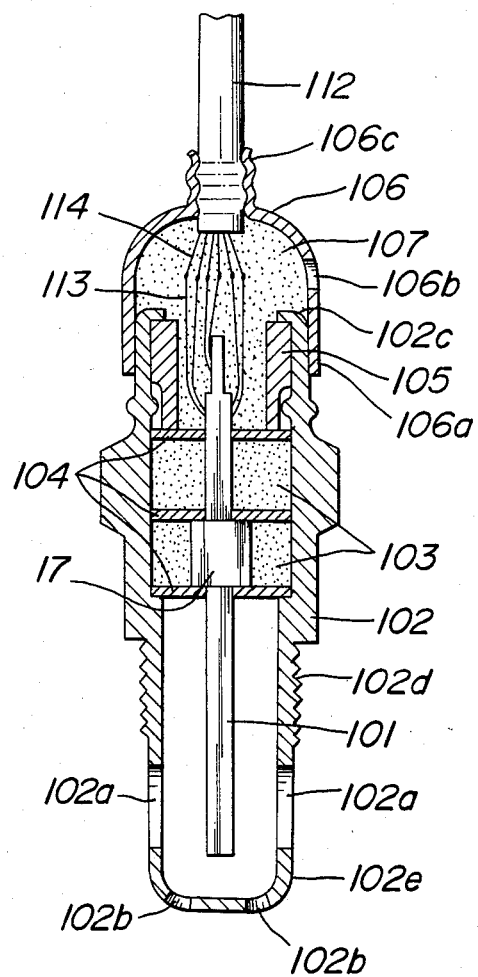
FIG. 11 is a sectional view of a probe in which the oxygen sensor of FIG. 1 is assembled.
Figure 12:
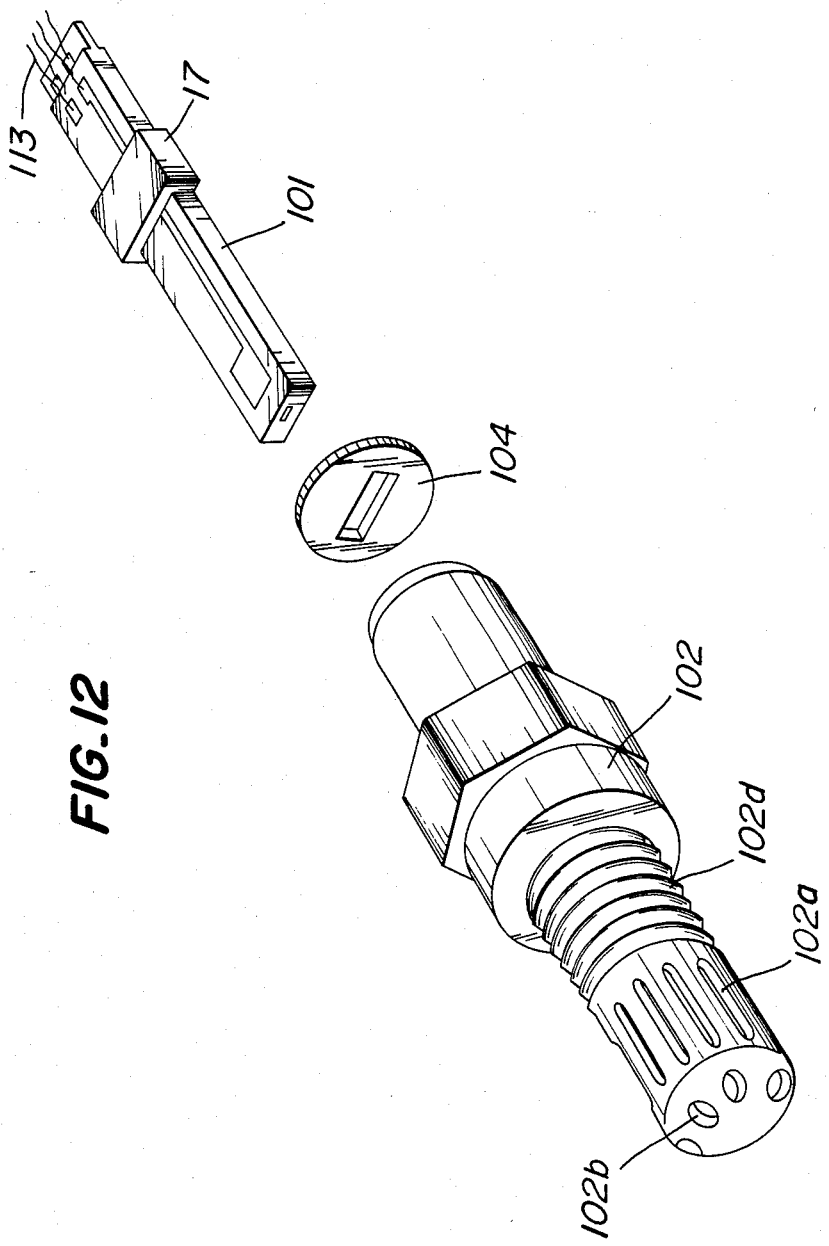
FIG. 12 is an explanatory diagram showing a method of assembling the probe of FIG. 11.

An example of oxygen sensor probes, which is assembled by using the above-mentioned first embodiment of the oxygen sensor, will be explained now by referring to FIG. 11. Front portion of an oxygen sensor 101 according to the first embodiment of the invention is inserted through a rectangular hole of an annular holder plate 104 until the coupling portion 17 of the oxygen sensor 101 engages the annular holder plate 104, as shown in FIG. 11 and FIG. 12. The oxygen sensor 101 with the annular holder plate 104 is inserted into a tubular housing 102 made of a suitable metallic material, so that the annular holder plate 104 rests on an inner shoulder portion of the housing 102. A ceramic adhesive 103 is filled between the coupling portion 17 of the oxygen sensor and the sidewall of the housing 102, and a second annular holder plate 104 is fitted to the oxygen sensor 101 as shown in FIG. 11. The ceramic adhesive 103 is again filled between the rear portion of the oxygen sensor 101 and the sidewall of the housing 102, and a third annular holder plate 104 is fitted to the oxygen sensor 101 in the housing 102 as shown in FIG. 11. A cylindrical spacer 105 is placed between the third annular holder plate 104 and the entry of the housing 102, and the edge portion 102c of the entry of the housing 102 is caulked so as to fix the oxygen sensor 101 in the housing 102.

The housing 102 has a shielding tube coaxially secured to front portion thereof so as to enclose the front portion of the oxygen sensor 101 with a spacing therefrom, and holes are bored through the sidewall of the shielding tube for limiting the flow of the gas being measured therethrough. The shielding tube may be formed as an integral part of the housing 102 or may be made separately and connected to the housing 102. In the example of FIG. 11, the shielding tube is a bottomed tube 102e integrally formed with the housing 102. The bottomed tube 102e has a number of sidewall openings 102a and bottom openings 102b for limiting the flow of exhaust gas or the gas being measured relative to the oxygen sensor 101.

Lead wires 113 emanating from the outlet portions at the rear end of the oxygen sensor 101 are connected to conductors 114 of an insulated cord 112, which cord 112 has the opposite end thereof connected to a measuring and processing unit (not shown). The core 112 is inserted through a cord inlet opening 106c of the metallic connector tube 106, and an enlarged opening 106a of the connector tube 106 is secured to the housing 102 in the proximity of the caulked edge 102c by spot welding or the like. After the cord inlet opening 106c is caulked to fasten the insulated cord 112 to the metallic connector tube 106, hardening synthetic resin fixer or heat-resisting inorganic adhesive material 107 is injected into the inside of the metallic connector tube 106 through a hole 106b thereof. Whereby, the oxygen sensor probe is assembled.

In operation, the oxygen sensor probe thus assembled is mounted onto an exhaust gas manifold or an exhaust gas return tube of an automobile engine, for instance by screwing the threaded portion 102d of the probe onto the sidewall of the manifold or the tube. The bottomed tube 102e, or the shielding tube, is to prevent the tip portion of the heater-mounted oxygen sensor 101 from being excessively cooled by the stream of the exhaust gas while allowing incoming flow of the exhaust gas or the gas being measured through the openings 102a and 102b.

In short, the oxygen sensor of the present invention measures the oxygen partial pressure in the gas or atmosphere being measured based on the fact that, when a steady balance of the oxygen flow and a steady distribution of the oxygen concentrations are established in the oxygen sensor, there is a functional relationship among the oxygen partial pressure in the gas being measured, the electric current through the oxygen pump element for pumping in or pumping out (this current directly relates to the amount of oxygen moving from the above-mentioned enclosed cavity to the gas being measured or vice versa through the oxygen pump element), and the output from the oxygen concentration cell element, which output gives the ratio between the oxygen partial pressure in the above-mentioned gap or the enclosed cavity communicating with the gas being measured through the above-mentioned passages and the oxygen partial pressure in the gas being measured, said ratio being determined by the well-known Nernst's equation. Accordingly, the method of the measurement by using the oxygen sensor of the invention is not restricted to the above-mentioned approach of varying the magnitude of the electric current through the oxygen pump element, but the oxygen sensor of the invention can be used by a different method, for instance by allowing the output from the oxygen concentration cell element to vary so as to represent the oxygen partial pressure of the gas being measured under the conditions that the pumping out electric current through the oxygen pump element is controlled at a constant value.

As described in detail in the foregoing, the oxygen sensor of the present invention uses an oxygen pump element having a first oxygen-ion-conductive solid electrolyte board with electrodes layers attached to opposite surfaces at one end of the first board; an oxygen concentration cell element having a second oxygen-ion-conductive solid electrolyte board disposed in parallel to said first board, said second board having electrode layers attached to opposite surfaces at one end thereof in alignment with said electrode layers of said first board; and an electrically insulating board inserted between said oxygen pump element and said oxygen concentration cell element, said insulating board having a hole bored through said insulating board so that a cavity is defined in the hole by being closed with said electrode layers attached to the opposing surface of the first board and the second board, and passages formed through said insulating board so as to communicate said cavity to outside of the oxygen sensor. A well insulated heat-generating resistor may be embedded in said insulating board along periphery of said hole thereof, or may be disposed on that side of the oxygen pump element which is opposite to the oxygen concentration cell element, whereby said oxygen sensor is selectively heated to such a temperature that said oxygen concentration cell element measures a ratio between oxygen concentration in said cavity and oxygen concentration of a gas surrounding the outside of said oxygen sensor while said oxygen pump element causes oxygen diffusion therethrough between said cavity and the outside of the oxygen sensor. Accordingly, the heating electric current through the heat-generating resistor is prevented from leaking into other elements, so that high measuring accuracy of the oxygen sensor, especially that of the oxygen concentration cell element, is ensured. Thus, the invention has succeeded in providing an efficient temperature control of the oxygen sensor.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. An oxygen sensor, comprising an oxygen pump element having a first oxygen-ion-conductive solid electrolyte board with electrode layers attached to opposite surfaces at one end of the first board; an oxygen concentration cell element having a second oxygen-ion-conductive solid electrolyte board disposed in parallel to said first board, said second board having electrode layers attached to opposite surfaces at one end thereof in alignment with said electrode layers of said first board; a heater element inserted between said oxygen pump element and said oxygen concentration cell element and consisting of an electrically insulating plate and heat-generating resistor disposed thereon; and an electrically insulating element inserted between said oxygen pump element and oxygen concentration cell element and disposed opposingly to said heat-generating resistor; each of said heater element and said electrically insulating element having a hole bored therethrough so as to define a cavity by closing said hole with said electrode layers attached to opposing surfaces of the first board and the second board, the length and width of said holes being approximately equal to the length and width of said electrode layers, said cavity having a thickness of approximately 0.5 mm taken as a spacing between said oxygen pump element and said concentration cell element; and further having at least one passage formed through said insulating element and said heater element so as to communicate said cavity to outside of the oxygen sensor, said passage having a cross-sectional area of at least 1 mm$^2$ and said passage having a thickness which is equal to the thickness of said cavity to prevent said passage from becoming plugged during use, said heat-generating resistor extending on said electrically insulating plate along the periphery of said cavity, wherein a unitary structure is made by overlaying and sintering of non-sintered green bodies of said oxygen concentration cell element, said heater element, said electrically insulating element and said oxygen pump element, whereby said oxygen sensor is selectively heated to a temperature such that said oxygen concentration cell element measures a ratio between oxygen concentration in said cavity and oxygen concentration of a gas surrounding the outside of said oxygen sensor while said oxygen pump element causes oxygen diffusion therethrough between said cavity and the outside of the oxygen sensor.

2. An oxygen sensor as set forth in claim 1, wherein said electrically insulating plate of the heater element is made of a material selected from the group consisting of alumina and spinel.

3. An oxygen sensor as set forth in claim 1, wherein said heat-generating resistor extends so as to define a substantially closed loop resistor surrounding said cavity.

4. An oxygen sensor as set forth in claim 1, wherein said oxygen sensor has only one said passage communicating said cavity to outside of the oxygen sensor.

5. An oxygen sensor as set forth in claim 1, wherein said electrically insulating element is an insulating coating.

6. An oxygen sensor as set forth in claim 1, wherein said electrodes and said heat-generating resistor are made of heat-resisting metallic layers formed by printing with a paste containing the heat-resisting metal and sintering the thus printed paste at the time of sintering the elements.

7. An oxygen sensor as set forth in claim 6, wherein said paste further contains green material powder which is the same material as that of the insulating plate.

8. An oxygen sensor, comprising an oxygen pump element having a first oxygen-ion-conductive solid electrolyte board with electrode layers attached to opposite surfaces at one end of the first board; and oxygen concentration cell element having a second oxygen-ion-conductive solid electrolyte board disposed in parallel to said first board, said second board having electrode layers attached to opposite surfaces at one end thereof in alignment with said electrode layers of said first board; an intermediate board element inserted between said oxygen pump element and said oxygen concentration cell element, said intermediate board element having a hole bored therethrough so as to define a cavity by closing said hole with said electrode layers attached to opposing surfaces of the first board and the second board, the length and width of said holes being approximately equal to the length and width of said electrode layers, said cavity having a thickness of approximately 0.5 mm taken as a spacing between said oxygen pump element and said concentration cell element; and at least one passage formed through said intermediate board element so as to communicate said cavity to outside of the oxygen sensor, said passage having a cross-sectional area of at least 1 mm² and said passage having a thickness which is equal to the thickness of said cavity to prevent said passage from becoming plugged during use; a heater element arranged on the top surface of said oxygen pump element and consisting of an electrically insulting plate and a heat-generating resistor disposed thereon at opposite side to said oxygen pump element; and a protective board element disposed on said heater element; each of said heater element and said protective boards element having a hole bored therethrough with substantially same dimension and alignment of those of the top electrode layer of said oxygen pump element so as to expose said top electrode layer of said oxygen pump element, said heat-generating resistor of said heater element extending on said electrically insulating plate along the periphery of said cavity, wherein said heat-generating resistor extends so as to define a substantially closed loop resistor surrounding said hole of said heater element, and a unitary structure is made by overlaying and sintering of non-sintered green bodies of said oxygen concentration cell element, said intermediate board element, and oxygen pump element, said heater element and said protective board element, whereby said oxygen sensor is selectively heated to a temperature such that said oxygen concentration cell element measures a ratio between oxygen concentration in said cavity and oxygen concentration of a gas surrounding the outside of said oxygen sensor while said oxygen pump element causes oxygen diffusion therethrough between said cavity and the outside of the oxygen sensor.

9. An oxygen sensor as set forth in claim 8, wherein said electrically insulating plate of the heater element is made of a material selected from the group consisting of alumina and spinel.

10. An oxygen sensor as set forth in claim 8, wherein said intermediate board element is made of a material selected from the group consisting of alumina, spinel and a solid electrolyte board similar to those of said oxygen pump element and said oxygen concentration cell element.

11. An oxygen sensor as set forth in claim 8, wherein said oxygen sensor has a plurality of said passages communicating said cavity to outside of the oxygen sensor.

12. An oxygen sensor as set forth in claim 8, which has a unitary structure made by overlaying and sintering of said oxygen concentration cell element, said intermediate board element, said oxygen pump element, said heater element and said protective board element with a heat-resisting inorganic adhesive.

13. An oxygen sensor as set forth in claim 8, wherein said electrodes and said heat-generating resistor are made of heat-resisting metallic layers formed by printing with a paste containing the heat-resisting metal and sintering the thus printed paste at the time of sintering the elements.

14. An oxygen sensor as set forth in claim 13, wherein said paste further contains green material powder which is the same material as that of the insulating plate.

15. An oxygen sensor, comprising:
an oxygen pump element having a first oxygen-ion-conductive solid electrolyte board electrode layers attached to opposite surfaces at one end of the first board;
an oxygen concentration cell element having a second oxygen-ion-conductive solid electrolyte board disposed in parallel to said first board, said second board having electrode layers attached to opposite surfaces at one end thereof in alignment with said electrode layers of said first board;
a heater element inserted between said oxygen pump element and said oxygen concentration cell element and consisting of an electrically insulating plate and heat-generating resistor disposed thereon;
an electrically insulating element inserted between said oxygen pump element and oxygen concentration cell element and disposed opposingly to said heat-generating resistor;
each of said heater element and said electrically insulating element having a hole bored therethrough so as to define a cavity by closing said hole with said electrode layers attached to opposing surfaces of the first board and the second board, the length and width of said holes being approximately equal to the length and width of said electrode layers, said cavity having a thickness of approximately 0.5 mm taken as a spacing between said oxygen pump element and said concentration cell element; and further having at least one passage fromed through said insulating element and said heater element so as to communicate said cavity to outside of the oxygen sensor, said passage having a cross-sectional area of at least 1 mm² and said passage having thickness which is equal to the thickness of said cavity to prevent said passage from becoming plugged during use,
an insulated heat-generating resistor disposed adjacent to said oxygen pump element so as to extend along periphery of said cavity, and
another electrically insulating element disposed on that surface of said oxygen pump element which is opposite to said oxygen concentration cell element, said other insulating element having a hole corresponding to said electrode on said oxygen pump element, and said insulated heat-generating resistor is disposed on said other insulating element so as to surround said hole thereof; wherein said heat-generating resistor is disposed on said insulating element along periphery of said hole thereof so as to face said oxygen pump element, and an insulating coating is provided on said heat-generating resistor so as to insulate the heat-generating resistor from the oxygen pump element; whereby said oxygen sensor is selectively heated to such a temperature that said oxygen concentration cell element measures a ratio between oxygen concentration in said cavity and oxygen concentration of a gas surrounding the outside of said oxygen sensor while said oxygen pump element causes oxygen diffusion therethrough between said cavity and the outside of the oxygen sensor.

16. An oxygen sensor, comprising an oxygen pump element having a first oxygen-ion-conductive solid electrolyte board with electrode layers attached to opposite surfaces at one end of said first board; an oxygen concentration cell element having a second oxygen-ion-conductive solid electrolyte board disposed in parallel to said first board, and said second board having electrode layers attached to opposite surfaces at one end thereof in alignment with said electrode layers of said first board; a heater element inserted between said oxygen pump concentration cell element and consisting of an electrically insulating plate and heat-generating resistor disposed thereon; and an electrically insulating element inserted between said oxygen pump element and oxygen concentration cell element and disposed opposingly to said heat-generating resistor; each of said heater element and said electrically insulating element having a hole bored therethrough so as to define a cavity by closing said hole with said electrode layers attached to opposing surfaces of the first board and the second board, the length and width of said holes being approximately equal to the length and width of said electrode layers, said cavity having a thickness of approximately 0.5 mm taken as a spacing between said oxygen pump element and said concentration cell element; and further having at least one passage formed through said insulating element and said heater element so as to communicate said cavity to outside of the oxygen sensor, said passage having a cross-sectional area of at least 1 mm$^2$ and said passage having a thickness which is equal to the thickness of said cavity to prevent said passage from becoming plugged during use, said heat generating resistor extending on said electrically insulating plate along the periphery of said cavity, whereby said oxygen sensor is selectively heated to a temperature such that said oxygen concentration cell element measures a ratio between oxygen concentration in said cavity and oxygen concentration of a gas surrounding the outside of said oxygen sensor while said oxygen pump element causes oxygen diffusion therethrough between said cavity and the outside of the oxygen sensor.

* * * * *